(12) United States Patent
Ouari et al.

(10) Patent No.: US 8,648,193 B2
(45) Date of Patent: Feb. 11, 2014

(54) DINITROXIDE-TYPE BIRADICAL COMPOUNDS OPTIMIZED FOR DYNAMIC NUCLEAR POLARIZATION (DNP)

(75) Inventors: Olivier Ouari, Seynod (FR); Hakim Karoui, Marseille (FR); Francois Le Moigne, Marseille (FR); Paul Tordo, Marseille (FR); Robert G. Griffin, Newton, MA (US); Yoh Matsuki, Osaka (JP); Thorsten Maly, Cambridge, MA (US)

(73) Assignee: Universite d'Aix Marseille (FR)

( * ) Notice: Subject to any disclaimer, the term of this patent is extended or adjusted under 35 U.S.C. 154(b) by 373 days.

(21) Appl. No.: 12/474,326

(22) Filed: May 29, 2009

(65) Prior Publication Data

US 2010/0249386 A1 Sep. 30, 2010

(30) Foreign Application Priority Data

Mar. 26, 2009 (FR) ..................................... 09 01454

(51) Int. Cl.
| | | |
|---|---|---|
| *C07D 235/02* | (2006.01) | |
| *C07D 207/46* | (2006.01) | |
| *C07D 263/52* | (2006.01) | |
| *C07D 409/02* | (2006.01) | |
| *C07D 409/14* | (2006.01) | |

(52) U.S. Cl.
USPC ........... 546/18; 548/216; 548/300.7; 548/407

(58) Field of Classification Search
USPC ........................................................ 546/18
See application file for complete search history.

(56) References Cited

U.S. PATENT DOCUMENTS

| | | | |
|---|---|---|---|
| 3,840,494 | A | 10/1974 | Murayama et al. |
| 4,921,962 | A | 5/1990 | Galbo et al. |
| 5,204,473 | A | 4/1993 | Winter et al. |
| 2004/0082742 | A1 | 4/2004 | Nesvadba et al. |
| 2005/0107696 | A1 | 5/2005 | Griffin et al. |
| 2006/0149011 | A1 | 7/2006 | Nesvadba et al. |

FOREIGN PATENT DOCUMENTS

| | | |
|---|---|---|
| FR | 1526656 | 5/1968 |
| JP | 4362632 | 12/1992 |

OTHER PUBLICATIONS

Galbo, et al. Document No. 113:152265 retrieved from Caplus (1990).*

Nesvadba, et al. Accession No. 2006:175561 retrieved from Caplus (2006).*

Hu, Kan-Nian, Yu, Hsiao-Hua, Swager, Timothy M., Griffin, Robert G., "Dynamic Nuclear Polarization with Biradicals", "Journal of the American Chemical Society", Aug. 14, 2004, vol. 126, pp. 10844-10845.

Song, Changsik, Hu, Kan-Nian, Joo, Chan-Gyu, Swager, Timothy M., Griffin, Robert G., "Totapol: A Biradical Polarizing Experiments in Aqueous Media", "Journal of the American Chemical Society", Aug. 16, 2006, vol. 128, pp. 11385-11390.

Hu, Kan-Nian, Song, Changsik, Yu, Hsiao-Hua, Swager, Timothy M., Griffin, Robert G., "High-frequency Dynamic Nuclear Polarization Using Biradicals: A Mutlifrequency EPR Linshape Analysis", "American Institute of Physcis", Jan. 23, 2008, vol. 128, pp. 052302-1 - 052302-17.

Michon, J. et al.; "Nitroxides-88: ESR Conformational Study of a Biradical", "Tetrahedron", 1980, pp. 871-876, Vol. 36, No. 7.

Miller, Joel S. et al; "Organic and Organometallic Molecular Magnetic Materials—Designer Magnets", "Angew. Chem., Int. Ed. Engl. ", 1994, pp. 385-415, vol. 33, No. 4.

Hu, Kan-Nian et al.; "Dynamic Nuclear Polarization with Biradicals", "Journal of the American Chemical Society", 2004, pp. 10844-10845, vol. 126, No. 35.

Song, Changsik et al; "Totapol: A Biradical Polarizing Agent for Dynamic Nuclear Polarization Experiments in Aqueous Media", "Journal of the American Chemical Society", 2006, pp. 11385-11390, vol. 128, No. 35.

Joo, Chan-Gyu et al.; "In Situ Temperature Jump High-Frequency Dynamic Nuclear Polarization Experiments: Enhanced Sensitivity in Liquid-State NMR Spectroscopy", "Journal of the American Chemical Society", 2006, pp. 9428-9432, vol. 128, No. 29.

Hu, Kan-Nian et al.; "High-frequency Dynamic Nuclear Polarization Using Biradicals: A Multifrequency EPR Lineshape Analysis", "Journal of the American Chemical Society", 2008, pp. 052302-1 - 052302-18, vol. 128, No. 5.

Chiarelli, R. et al; "Synthese du dupeyredioxyle (1,3,5,7-tetramethl-2, 6-diazaadamantane-2, 6-dioxyle), biradical nitroxyde a properietes ferromagnetiques", "Bulletin de la Societe Chimique de France, Societe Francaise de Chimie", Jan. 1, 2001, pp. 299-303, vol. 130, No. 3.

Rassat, Andre; "Magnetic Properties of Nitroxide Multiradicals", "Pure and Applied Chemistry", 1990, pp. 223-227, vol. 62, No. 2.

(Continued)

*Primary Examiner* — Shawquia Young
(74) *Attorney, Agent, or Firm* — Lackenbach Siegel, LLP

(57) ABSTRACT

The present invention relates to the field of organic chemistry and in particular to organic free radicals used as polarizing agents in the technique of Dynamic Nuclear Polarization (DNP), which involves transferring the polarization of electron spins to the nuclei of a compound whose Nuclear Magnetic Resonance (NMR) is being observed. It concerns dinitroxide-type biradical polarizing agents characterized by a rigid linkage between the nitroxide units that enables optimal orientation and distance to be maintained between the aminoxyl groups of said nitroxide units. This particular structure enables, at low temperatures and high fields, optimal transfer of polarization and optimal enhancement of NMR/MAS signals of the polarized nuclei of the compound studied.

13 Claims, 4 Drawing Sheets

(56) References Cited

OTHER PUBLICATIONS

Huang, Wenli et al; "Unique Behavior of Nitroxide Biradicals in the Controlled Radical Polymerization of Styrene", "Macromolecules", 2002, pp. 2305-2317, vol. 35, No. 6.

Toda, Toshimasa et al.; "Studies on Stable Free Radicals. XI. ESR Spectra of Stable Nitroxide Biradicals", Bulletin of the Chemical Society of Japan, 1972, pp. 1764-1766, vol. 45, No. 6.

Toda, Toshimasa et al.; "Studies on Stable Free Radicals. VI. Synthesis of Substituted 4-Imidazolidinone-1-oxyls", "Bulletin of the Chemical Society of Japan", 1971, pp. 3445-3450, vol. 45, No. 6.

Gagnaire, Genevieve et al.; "Regulation by Potassium Ions of Spin Exchange and Dipolar Splitting in a Biradical. A Simple Allosteric System", "Tetrahedron Letters", 1989, pp. 6507-6510, vol. 30, No. 47.

Dupeyre, Rose-Mare et al.: "Nitroxides. LII. Synthesis and electron spin resonance studies of N,N'-dioxy-2,6- diazaadamantane, a Symmetrical Ground State Triplet", "Journal of the American Chemical Society", 1974, pp. 6559-6568, vol. 96, No. 21.

Fluekiger, P. et al; "Chirality and Spin Density: Ab initio and Density Functional Approaches", "International Journal of Quantum Chemistry", 1993, pp. 649-663, vol. 45, No. 6.

\* cited by examiner

Two nitroxide units examples     Aminoxyl group and its nodal plan P

DINITROXIDE-TYPE BIRADICAL COMPOUNDS OPTIMIZED FOR DYNAMIC NUCLEAR POLARIZATION (DNP)

The present invention relates to the field of organic chemistry and in particular to organic free radicals used as polarizing agents in the technique of Dynamic Nuclear Polarization (DNP), which involves transferring the polarization of electron spins to the nuclei of a compound whose Nuclear Magnetic Resonance (NMR) is being observed. It concerns polarizing agents that have a particular molecular structure that enable, at low temperatures and high fields, the optimal transfer of polarization and optimal enhancement of NMR/MAS signals of the polarized nuclei in the compound being studied. Once the solid study sample has been polarized, it can be dissolved and if nuclear relaxation is not too rapid we obtain a "hyperpolarized" solution of the sample, which can be used for NMR liquid phase or nuclear Magnetic Resonance Imaging (MRI) observations.

Several mechanisms are involved in low-temperature DNP, and of them, "cross effect" (CE) and "thermal mixing" allow for maximum polarization and thus maximum enhancement of NMR signals. These two mechanisms are essentially based on a three-spin process, two electron spins $S_1$ and $S_2$ coupled across a dipole/dipole interaction and spin I of nucleus n which we want to polarize (FIG. 1). If we pump the sample to the frequency of $\omega_1/2\pi$ and if the frequency $\omega_2/2\pi$ is such that the difference ($\omega_2/2\pi - \omega_1/2\pi$) is equal to the Larmor frequency ($\omega_n/2\pi$) of nuclei n, a flip-flop mechanism engaging the three spins and conserving energy results in the polarization of these nuclei.

Stable nitroxides like TEMPO are commonly used polarizing agents in high-field, solid-phase DNP. With concentrations of TEMPO on the order of 40 mM, augmentation factors of polarization, $\epsilon$, on the order of 40 have been observed for the $^{13}C$ urea nucleus. If the concentration is decreased, the augmentation factor falls rapidly as the $S_1$ dipole/$S_2$ dipole interaction becomes less efficient. R. G. Griffin demonstrated (R. G. Griffin et al.: J. Am. Chem. Soc. 126, 10844-10845, 2004) that if the two spins $S_1$ and $S_2$ are introduced in the same molecule, the nuclear polarization obtained is more efficient, even for lower concentrations of polarizing agent. He used various dinitroxides (FIG. 2) formed by two TEMPO units connected via different types of linking arms, such as bis-TEMPO-n-ethylene glycol (BTnE) (n indicates the number of ethylene glycol units), bis-TEMPO-Urea (BTurea), bis-TEMPO-oxalamide (BTOXA) and in particular 1-(TEMPO-4-oxy)-3-(TEMPO-4-amino)propan-2-ol (TOTAPOL).

The polarization enhancement factors observed (at 90 K, for a field of 5 T and an irradiation strength of 1.5 W) for the nucleus of $^{13}C$ urea (R. G. Griffin et al: J. Am. Chem. Soc., 128, 11385-11390, 2006; J. Chem. Phys., 128, 052302-1/052302-17, 2008) went from $\epsilon=175\pm20$ with BT2E (5 mM) or $\epsilon=190\pm20$ with TOTAPOL (5 mM), whereas $\epsilon=40\pm5$ only with TEMPO (40 mM).

In theory, for these dinitroxides under the working conditions used, the equality of $\omega_2/2\pi - \omega_1/2\pi = \omega_n/2\pi$ will be practically verified for molecules that adopt a conformation in which the nodal plans of the π systems of the two aminoxyl groups create nearly a 90° angle between them. This is a result of the strong anisotropy of TEMPO's Landé g-factor ($g_{xx}=2.0090$; $g_{yy}=2.0061$; $g_{zz}=2.0021$). However, these molecules have no particular structural constraints allowing the molecular geometry to be blocked such that the nodal plans of the two aminoxyl groups of the two nitroxyl units create an angle near 90° between them. Thus, the flexibility of the linkage between the two nitroxide units of these various nitroxides does not favor optimal polarization.

The object of the present invention is to provide dinitroxide-type compounds that have a particular linkage between the two cycles whose characteristics ensure a consistent optimal transfer of polarization in DNP. The present invention thus meets the needs of polarizing agents that enable the optimal transfer of polarization in DNP in order to enhance NMR performance in solid or liquid phase and MRI performance.

In the description of the present invention, the terms "nitroxide unit" and "aminoxyl group" refer to the entities described in FIG. 3, which shows two examples of nitroxide units and an aminoxyl group in its nodal plan P.

The present invention concerns dinitroxide-type polarizing agents in which the two aminoxyl groups belong to cycles, additionally, the linkage between the two aminoxyl groups constitutes a linkage that allows:

The distance between the aminoxyl groups to be fixed, which allows the dipole-dipole interaction to be controlled.

The angle created between the nodal plans of the two aminoxyl groups to be maintained near 90° (FIG. 4).

In a first object, the present invention concerns biradical dinitroxyde-type compounds. These dinitroxyde-type compounds are characterized in that they have a rigid linkage between the nitroxide units, with said rigid linkage between the aminoxyl groups being a linkage selected from:
  an arm comprising an odd number of spiranic bonds,
  an allenic linkage,
  a type of linkage found in certain polycyclic molecules implying orthogonality of the nodal plans of the two nitroxide units. For example:

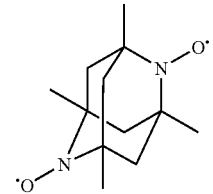

Furthermore, the dinitroxide-type compounds of the present invention are characterized in that the linkage connecting the nitroxide units allows for a stable conformation that maintains the angle created between the nodal plans of the aminoxyl groups of the two units $P_1$ and $P_2$ (FIG. 4), in an inclusive range between 65° and 115°.

In addition, the dinitroxide-type biradical compounds of the present invention are characterized in that their linkage allows nitrogen atoms from the aminoxyl groups comprised in the nitroxide groups to be maintained at a distance of between 3 Å and 16 Å.

Preferably, the nitroxide units that constitute the dinitroxide biradical compounds of the present invention are selected from among piperidinoxyl, pyrrolidinoxyl, imidazolinoxyl, imidazolidinoxyl, oxazolidinoxyl and nitronylnitroxide units.

In another preferred mode of the invention, the nitroxide-type biradical compounds of the present invention are characterized by the addition of at least one chemical group. In a specific mode of this preferred mode, the chemical group or groups added to the biradical compounds of the present invention facilitate the solubility in water of said biradical compounds and are selected from the group composed, for example, of the following functions and groups: hydroxyl (—OH), primary amine (—NH$_2$), secondary amine (—NH), tertiary (—N), ammonio (—N$^+$), amine oxide (—NO), carboxyl (—COOH), sulfanyl (—SH), polyethylene-glycol (CH$_2$—CH$_2$—O)n-CH$_2$X, X=OH, NH$_2$) sulfinyl (—SO), sulfonyl (—SO$_2$), sulfonato (—SO$_3^-$), phosphono (—PO$_3$H$_2$, —PO$_3$R$_2$ where R=(C1-C17) alkyl, (C6-C18) aryl), phosphoryl (—P(O)R$_2$ where R=(C1-C17) alkyl, (C6-C18) aryl), phosphonio (—P$^+$), phosphoric ester (—O—PO$_3^-$). In another specific mode of this preferred mode of the invention, the biradical compounds of this invention are characterized in that they contain at least one photosensitizer selected from, for example, thioxanthone, benzoine, benzil dimethyl acetal, or benzophenone. In another specific mode of the invention, the chemical group or groups added to the biradical compounds of the present invention are reactive with respect to characteristic groups: —SH, —NH$_2$, —OH, —COOH, hydroxyaryl (ArOH) and allow the conjugation of said biradical compounds to the molecules of interest. These chemical groups are activated esters that have the following formulas, given as non-exhaustive examples:

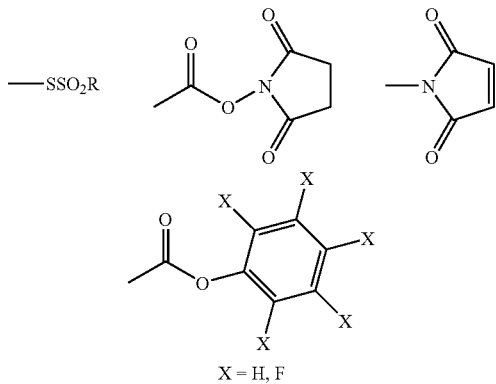

In a final specific mode of this preferred mode of the invention, the dinitroxide-type biradical compounds per this invention are characterized in that they are conjugated to biomolecules such as proteins, ribosomes, lipids, saccharides, DNA and RNA.

In another preferred mode of the invention, the dinitroxide compounds per the present invention are characterized by isotopic labeling. In a preferred embodiment, the dinitroxide compounds are isotopically labeled by Deuterium ($^2$H). In another preferred embodiment, the dinitroxide compounds are isotopically labeled by Nitrogen 15 ($^{15}$N). In another preferred embodiment, the dinitroxide compounds are isotopically labeled by Carbon 13 ($^{13}$C).

In a final preferred mode of the invention, the compounds of the present invention are paramagnetic compounds that comprise at least one dinitroxide representation composed of two nitroxide units connected by a rigid linkage as claimed in the present invention.

In a second object, the present invention also concerns a composition that comprises at least one of the dinitroxide compounds mentioned in the preceding embodiments.

In a third object, the present invention also concerns the use of at least one of the dinitroxide compounds detailed in the preceding embodiments as a polarizing agent. In a preferred mode, the invention concerns the use of at least one of the dinitroxide compounds of the present invention as a polarizing agent in the techniques of structural biology, Nuclear Magnetic Resonance of solids or applied to liquid samples, particle physics, and medical imaging. In a more preferred mode, the invention concerns the use of at least one of the dinitroxide compounds of the present invention as a polarizing agent in DNP.

Preferably, the invention concerns the use of compounds of the general formulae:

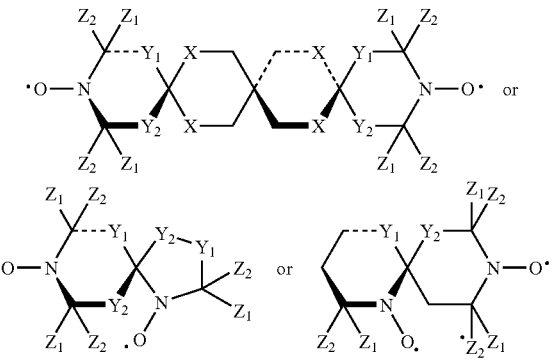

in which X is a single bond between the atoms n−1 and n+1, or O, N, N(O), S, S(O), SO$_2$, or a (C1-C4) alkyl chain and Y1 is a single bond between the atoms n−1 and n+1, or O, N, N(O), S, S(O), SO$_2$, or a (C1-C4) alkyl chain, and Y2 is a single bond between the atoms n−1 and n+1, or O, N, N(O), S, S(O), SO$_2$, or a (C1-C4) alkyl chain and Z$_1$=—R$_1$ or —R$_1$-R$_2$ and Z$_2$=—R$_1$ or —R$_1$-R$_2$, where R$_1$ is a chain of (C1-C17) alkyl, cycloalkyl, heterocycloalkyl, spirocycloalkyl, spiroheterocycloalkyl, alkenyl, alkynyl, (C6-C18) aryl and R$_2$=H or has a function and group from the following: hydroxyl (—OH), primary amine (—NH$_2$), secondary amine (—NH), tertiary (—N), ammonio (—N$^+$), amine oxide (—NO), carboxyl (—COOH), sulfanyl (—SH), polyethylene-glycol (CH$_2$—CH$_2$—O)n-CH$_2$X, X=OH, NH$_2$) sulfinyl (—SO), sulfonyl (—SO$_2$), sulfonato (—SO$_3^-$), phosphono (—PO$_3$H$_2$, —PO$_3$R$_2$, where R=(C1-C17) alkyl, (C6-C18) aryl), phosphoryl (—P(O)R$_2$ where R=(C1-C17) alkyl, (C6-C18) aryl), phosphonio (—P$^+$), phosphoric ester (—O—PO$_3^-$).

In another preferred manner, the invention concerns the use of compounds of the general formula:

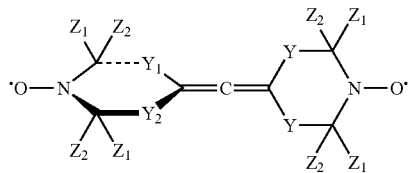

in which X is a single bond between the atoms n−1 and n+1, or O, N, N(O), S, S(O), SO$_2$, or a (C1-C4) alkyl chain and Y1 is a single bond between the atoms n−1 and n+1, or O, N, N(O), S, S(O), SO$_2$, or a (C1-C4) alkyl chain, and Y2 is a single bond between the atoms n−1 and n+1, or O, N, N(O), S, S(O), SO$_2$, or a (C1-C4) alkyl chain and Z$_1$=—R$_1$ or —R$_1$-R$_2$ and Z$_2$=—R$_1$ or —R$_1$-R$_2$, where R$_1$ is a chain of (C1-C17) alkyl, cycloalkyl, heterocycloalkyl, spirocycloalkyl, spiroheterocycloalkyl, alkenyl, alkynyl, (C6-C18) aryl and R$_2$=H or has a function and group from the following: hydroxyl (—OH), primary amine (—NH$_2$), secondary amine (—NH), tertiary (—N), ammonio (—N$^+$), amine oxide (—NO), carboxyl (—COOH), sulfanyl (—SH), polyethylene-glycol $(CH_2—CH_2—O)n-CH_2X$, $X=OH$, $NH_2$) sulfinyl (—SO), sulfonyl (—SO$_2$), sulfonato (—SO$_3^-$), phosphono (—PO$_3$H$_2$, —PO$_3$R$_2$ where R=(C1-C17) alkyl, (C6-C18) aryl), phosphoryl (—P(O)R$_2$ where R=(C1-C17) alkyl, (C6-C18) aryl), phosphonio (—P$^+$), phosphoric ester (—O—PO$_3^-$).

In another preferred manner, the invention concerns the use of compounds of the general formula:

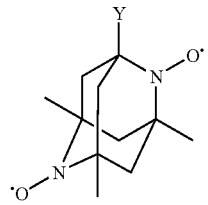

in which Y has no limitations.

By nitroxide unit, we mean a cycle with several atoms comprising an aminoxyl group.

By dinitroxide-type biradical compounds, or dinitroxide compounds, we mean compounds comprising two aminoxyl groups included, respectively, in the two separate nitroxide units defined previously.

Preferably, the nitroxide units that make up the dinitroxide biradical compounds of the present invention are selected from among units of piperidinoxyl, pyrrolidinoxyl, imidazolinoxyl, imidazolidinoxyl, oxazolidinoxyl and nitronylnitroxide. The dinitroxide-type biradical compounds of the present invention may be made up of homologous nitroxide units such as two piperidinoxyl units, two pyrrolidinoxyl units, two imidazolidinoxyl units, two oxazolidinoxyl units, two imidazolidinoxyl units or two nitronylnitroxide units. For example, the biradical compounds of the present invention may be made up of two tetramethylpiperidinoxyl units as in the following compound:

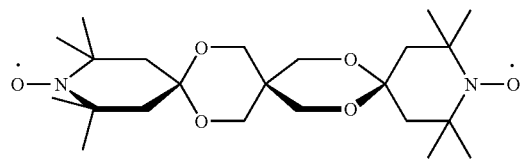

The nitroxide-type biradical compounds of the present invention may be made up of heterologous nitroxide units from among the nitroxide units mentioned above. For example, the biradical compounds of the present invention may be made up of, first, one tetramethylpiperidinoxyl unit and second, one oxazolidinoxyl unit as in the following compound:

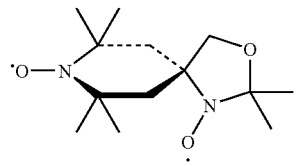

The dinitroxide-type biradical compounds of the present invention may constitute a representation included in a polynitroxide compound that comprises three, four, five, ten or n nitroxide units.

Figure 1:
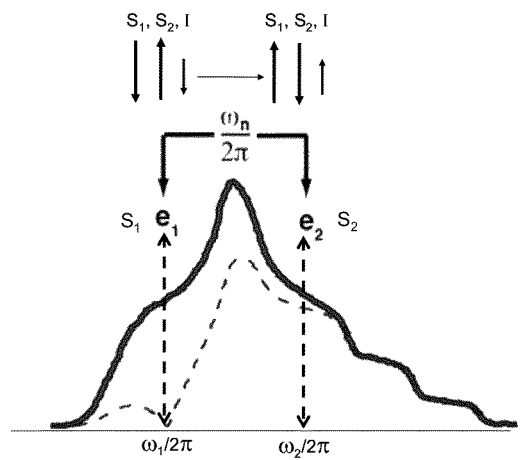
FIG. 1: EPR spectrum of the TEMPO radical in solid phase and illustration of a three-spin flip-flop process, with conservation of energy resulting in the polarization of nuclei n of spin I.
Figure 2:
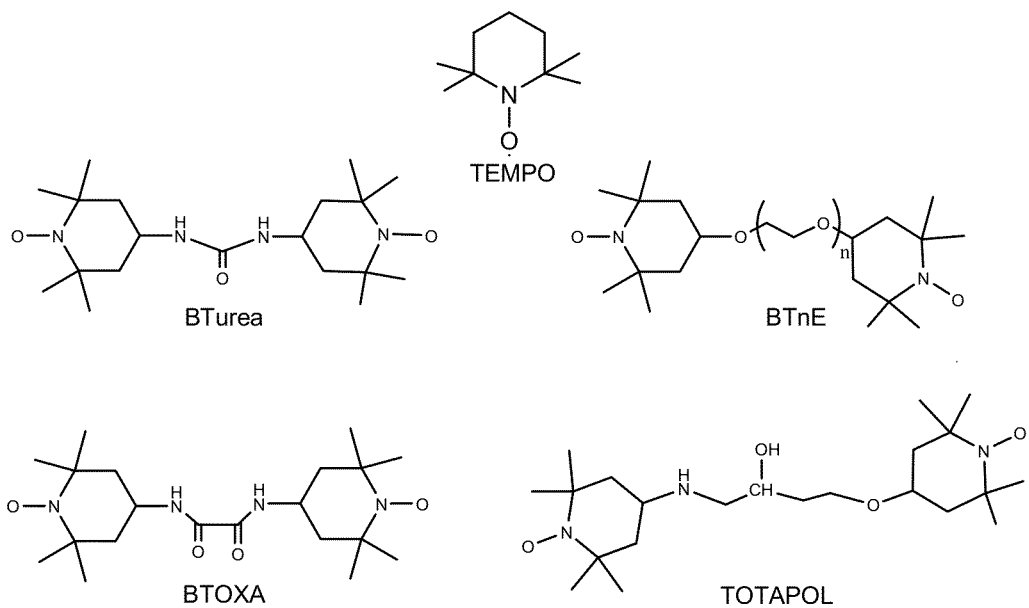
FIG. 2: TEMPO and dinitroxydes used by R. G. Griffin as polarizing agents in DNP experiments in solid phase at low temperature (T≤90 K).
Figure 3:
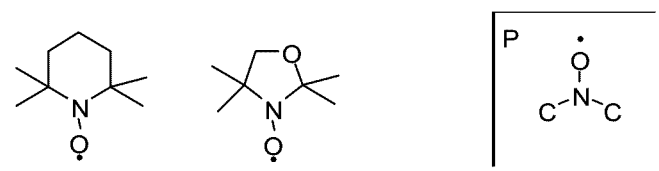
FIG. 3: Two examples of nitroxide units and an aminoxyl group in its nodal plan P.
Figure 4:
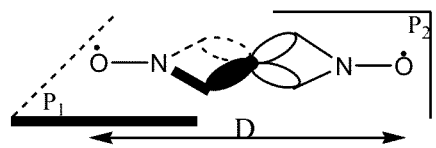
FIG. 4: Disposition of the nodal plans of the aminoxyl groups in the compounds of the invention.

The dinitroxide-type biradical compounds of this invention are characterized by a rigid linkage connecting the cycles that comprise the aminoxyl groups. The rigid linkage in the dinitroxide-type biradical compounds between the two aminoxyl groups allows the cycles containing these groups to be blocked in a conformation that maintains the angle created between them by their nodal plans P$_1$ and P$_2$ (FIG. 4), within an inclusive range between 65° and 115°. This linkage also allows the nitrogen atoms of the two aminoxyl groups to be maintained at a distance between 3 Å and 16 Å, which allows the dipole-dipole interaction to be controlled. The control of these two parameters in the dinitroxide compounds of the present invention enables optimal conditions to be obtained for the transfer of polarization.

The rigid linkage between the two aminoxyl groups per the present invention can be of three types selected from:
- an arm comprising an odd number of spiranic bonds,
- an allenic linkage,
- a type of linkage found in polycyclic molecules and implying orthogonality of the nodal plans of the two nitroxide units, e.g.:

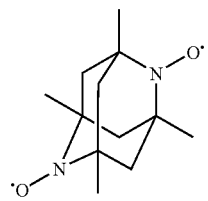

By spiranic bond, we mean a bond characterized by the presence of an atom included in two cycles or cyclic groups that are not accolated. An illustration of this type of bond is given below.

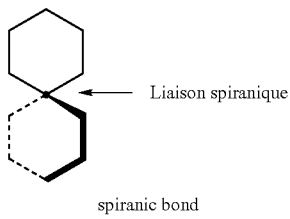

Liaison spiranique spiranic bond

This type of bond enables the cycles containing the nitroxide units in the biradical compounds of the present invention to be connected. This type of bond enables a rigid linkage to be formed between the cycles of said units and enables them to be blocked in a defined orientation favorable to the optimal transfer of polarization. By rigid linkage characterizing the compounds of the present invention, we also mean an odd number of successive spiranic bonds that enable the nitrogen atoms of the nitroxide units to be maintained at a distance that allows for optimal transfer of polarization. Preferably, the rigid linkage made up of one or more spiranic bonds allows the nitrogen atoms of the nitroxide units to be maintained at a distance of between 3 Å and 16 Å.

In a preferred mode of the present invention, the rigid linkage is made up of one, three or five successive spiranic bonds. In a more preferred mode, the rigid linkage is made up of one or three successive spiranic bonds. By arm comprising an odd number of spiranic bonds, we mean the rigid linkage that allows the nitroxide units of the biradical compounds of the present invention to be maintained both in a given conformation and at a given distance. In this same preferred embodiment, the rigid linkage made up of one or more spiranic bonds enables the nodal plans of the two aminoxyl groups of the dinitroxide-type biradical compounds of the present invention to be fixed relative to one another in an angle between 65° and 115°, inclusive. Preferably, this angle may be between 75° and 105°, or 85° and 95°. Even more preferably, the nodal plans of the two aminoxyl groups of the dinitroxide-type biradical compounds of the present invention are orthogonal.

An illustration of a rigid linkage made up of three spiranic bonds is given in the formula below:

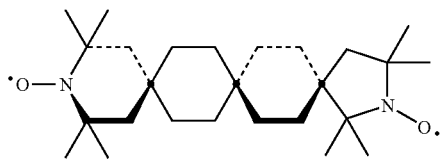

By allenic linkage, we mean a linkage that involves several carbon atoms where one of the carbon atoms of the molecule is connected to the two other carbon atoms by double bonds. An illustration of this type of bond is given in the following formula:

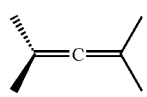

This type of allenic linkage allows the nitroxide units in the dinitroxide-type biradical compounds of the present invention to be connected. This type of linkage allows a rigid linkage to be formed between these cycles and allows them to be maintained in a stable conformation that is favorable to the optimal transfer of polarization as defined in the preceding paragraphs. In a preferred embodiment, the rigid linkage made up of an allenic linkage allows the nodal plans of the two aminoxyl groups of the nitroxide units of the dinitroxide-type biradical compounds of the present invention to be fixed relative to one another, in an angle between 65° and 115°, inclusive. Preferentially, this angle may be between 75° and 105°, or between 85° and 95°. Even more preferentially, the nodal plans of the two aminoxyl groups of the nitroxide units of the dinitroxide-type biradical compounds of the present invention are orthogonal. This type of linkage also enables the nitrogen atoms of the two nitroxide units to be maintained at a distance that enable an optimal transfer of polarization as defined in the preceding paragraphs. Preferentially, the rigid linkage made up of an allenic linkage enables the nitrogen atoms of the two nitroxide units to be maintained at a distance of between 3 Å and 16 Å.

Two illustrations of rigid linkages made up of an allenic linkage are given in the following formulae:

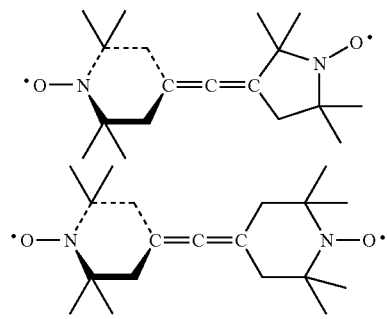

By polycyclic molecules with orthogonal nitroxide functions, we mean any molecule having at least two cycles each with a nitroxide unit and characterized in that it has a linkage made up of a polycyclic network that enables the nodal plans of the aminoxyl groups of the two nitroxide units to be maintained in a stable conformation that is favorable to the optimal transfer of polarization as mentioned in the preceding paragraphs. In particular, this linkage enables said nodal plans to be fixed in an orthogonal orientation. In other words, this type of linkage is found in certain polycyclic molecules that imply orthogonality in the nodal plans of the two nitroxide units. Equally, this linkage enables the nitrogen atoms of the nitroxide atoms to be maintained at a distance of between 3 Å and 16 Å, allowing for optimal transfer of polarization. This linkage belongs to the types of rigid linkages defined in the present invention.

An illustrative example of this type of linkage between two nitroxide units is given by the following formula:

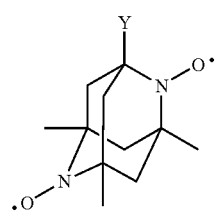

in which Y has no limitations.

The present invention thus proposes three types of rigid linkages (an arm composed of an odd number of spiranic bonds, an allenic linkage, a linkage in a polycyclic molecule with nitroxide units of which the aminoxyl groups have orthogonal nodal plans) that enable obtaining dinitroxide-type biradical compounds, composed of cycles containing two nitroxide units whose nodal plans are maintained in a fixed orientation that is favorable to the optimal transfer of polarization. Preferentially, these three types of rigid linkages enable the nodal plans of the two aminoxyl groups of the nitroxide units to be fixed relative to one another in an angle of between 65° and 115°, preferentially between 75° and 105°, or between 85° and 95°. In another preferred embodiment, the plans of the two nitroxide units of the compounds of the present invention are orthogonal. These three types of rigid linkages also enable the nitrogen atoms of the two nitroxide units to be maintained at a distance that allows for optimal transfer of polarization. Preferentially, these three types of linkages enable the nitrogen atoms of the two nitroxide units to be maintained at a distance between 3 Å and 16 Å.

The dinitroxide-type biradical compounds of the present invention are compounds comprised of two aminoxyl groups comprised respectively in cycles comprising 4, 5, 6, 7 and 8 atoms. These compounds can be represented by the following general formulae:

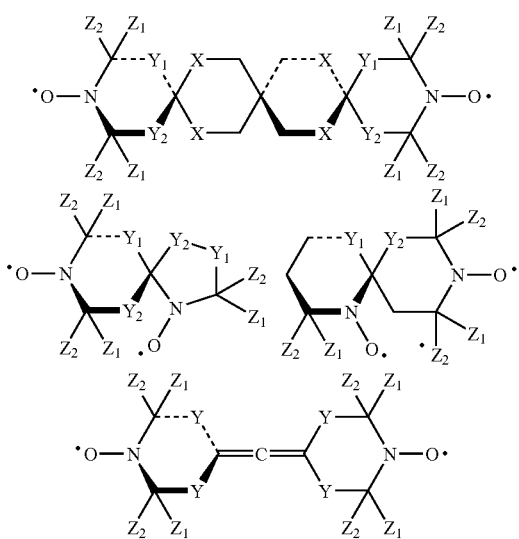

in which X is a single bond between the atoms n−1 and n+1, or O, N, N(O), S, S(O), SO$_2$, or a (C1-C4) alkyl chain and Y1 is a single bond between the atoms n−1 and n+1, or O, N, N(O), S, S(O), SO$_2$, or a (C1-C4) alkyl chain, and Y2 is a single bond between the atoms n−1 and n+1, or O, N, N(O), S, S(O), SO$_2$, or a (C1-C4) alkyl chain and Z$_1$=—R$_1$ or —R$_1$-R$_2$ and Z$_2$=—R$_1$ or —R$_1$-R$_2$, where R$_1$ is a chain of (C1-C17) alkyl, cycloalkyl, heterocycloalkyl, spirocycloalkyl, spiroheterocycloalkyl, alkenyl, alkynyl, (C6-C18) aryl and R$_2$=H or has a function and group from the following: hydroxyl (—OH), primary amine (—NH$_2$), secondary amine (—NH), tertiary (—N), ammonio (—N$^+$), amine oxide (—NO), carboxyl (—COOH), sulfanyl (—SH), polyethylene-glycol (CH$_2$—CH$_2$—O)n-CH$_2$X, X=OH, NH$_2$) sulfinyl (—SO), sulfonyl (—SO$_2$), sulfonato (—SO$_3^-$), phosphono (—PO$_3$H$_2$, —PO$_3$R$_2$ where R=(C1-C17) alkyl, (C6-C18) aryl), phosphoryl (—P(O)R$_2$ where R=(C1-C17) alkyl, (C6-C18) aryl), phosphonio (—P$^+$), phosphoric ester (—O—PO$_3^-$).

In a preferred embodiment, a compound according to the present invention is named bis-TEMPO-bis-Ketal (bTbK) and has the following formula:

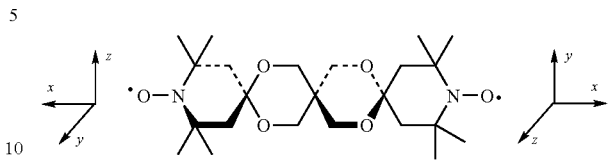

In another embodiment, the present invention concerns dinitroxide-type biradical compounds characterized by the properties discussed previously and by the fact that they also include chemical groups that facilitate their solubility in water. These groups that facilitate solubility in water enable the use of the biradical compounds of the present invention in aqueous media compatible with the use of compounds of the present invention in numerous biological applications. The biradical compounds of the present invention contain at least one such chemical group selected, as an example, from among the following functions and groups: hydroxyl (—OH), primary amine (—NH$_2$), secondary amine (—NH), tertiary (—N), ammonio (—N$^+$), amine oxide (—NO), carboxyl (—COOH), sulfanyl (—SH), polyethylene-glycol (CH$_2$—CH$_2$—O)n-CH$_2$X, X=OH, NH$_2$) sulfinyl (—SO), sulfonyl (—SO$_2$), sulfonato (—SO$_3^-$), phosphono (—PO$_3$H$_2$, —PO$_3$R$_2$ where R=(C1-C17) alkyl, (C6-C18) aryl), phosphoryl (—P(O)R$_2$ where R=(C1-C17) alkyl, (C6-C18) aryl), phosphonio (—P$^+$), phosphoric ester (—O—PO$_3^-$).

In another embodiment, the present invention concerns dinitroxide-type biradical compounds characterized by the properties discussed previously and by the fact that they also are composed of chemical groups that are reactive with respect to characteristic groups —SH, —NH$_2$, —OH, —COOH and hydroxyaryl (ArOH). These chemical groups enable the conjugation of dinitroxide-type biradical compounds of this invention to simple or complex molecules for analytical purposes. By simple molecules to which the biradical compounds of the present invention can be conjugated, we mean molecules that are made up of at least one photosensitizing group such as, for example, thioxanthone, benzoine, benzil dimethyl acetal or benzophenone. By complex molecules to which the biradical compounds of the invention can be conjugated, we mean mainly biomolecules such as proteins [structural, receptors, signaling, cellular transcription machinery (polymerases), cellular translation machinery (ribosomes)], lipids, saccharides, deoxyribonucleic acids (DNA) and ribonucleic acids (RNA). Four examples of chemical groups that allow the conjugation of the biradical compounds chemical groups that allow the conjugation of the biradical compounds of the present invention are given below, although this list is not exhaustive:

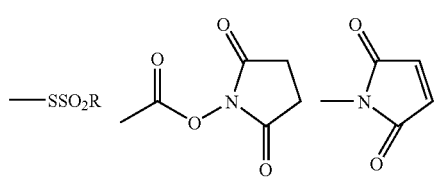

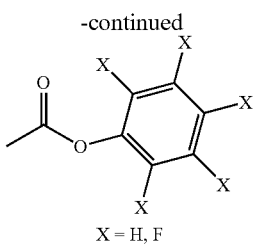

X = H, F

By isotopically labeled compounds, we include all derivatives of dinitroxide-type biradical compounds concerned by the scope described previously in this invention, obtained by radioisotope labeling of the various elements useful in the techniques of dynamic nuclear polarization, structural biology, Nuclear Magnetic Resonance of solids or applied to liquid samples, particle physics and medical imaging. The main elements that can label the biradical compounds of the present invention are Deuterium ($^2$H), Nitrogen 15 ($^{15}$N) and Carbon 13 ($^{13}$C), although this list is not limiting.

By composition, we include all solutions or injectable or non-injectable formulations, assimilable or non-assimilable, which contain one of the dinitroxide-type biradical compounds of the present invention in pure form or in combination with one or more other products, that is, any mixture comprising a certain percentage of at least one of the dinitroxide-type biradical representations described in the present invention. It is understood that these mixtures and compositions concern the derivatives of the dinitroxide biradical compounds of the present invention, such as derivatives with an added chemical group, derivatives conjugated to a molecule of interest, or the polynitroxide derivatives of these compounds. Mixtures formed of compounds and/or derivatives of these compounds of the invention and excipients are also included in the scope of the invention, as are liquid, solid, gel or other forms of these mixtures.

By use, we include any use that can be made of the compounds included in the scope of the invention. The principal use of the compounds of the invention concerns their use as polarizing agents in techniques such as Dynamic Nuclear Polarization but also in techniques such as Nuclear Magnetic Resonance of solids or applied to liquid samples. The use of compounds of the present invention covers the fields of chemistry, biology through the techniques of structural biology, as well as the field of physics through particle physics techniques. The use of compounds of the invention concerns the medical field, mainly that of medical imaging, such as the use of compounds of the invention in MRI as well as in diagnostics.

Example of Preparation and Use in Dynamic Nuclear Polarization of a Dinitroxide-Type Biradical Compound of the Present Invention: the Case of bTbK

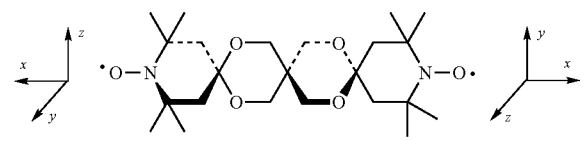

Preparation of the Diamine Precursor of bTbk

A mixture of 2,2,6,6-tetramethyl-4-piperidone (2.00 g, 12.8 mmoL), pentaerythritol (0.87 g, 6.4 mmoL) and p-toluenesulfonic acid (2.21 g, 12.8 mmoL) in 50 mL of toluene is set to reflux for 12 h, and the water formed is eliminated using a Dean-Stark trap. After cooling the mixture, it is washed with a 1N solution of NaOH (20 mL), then 20 mL of water. The organic solution is dried on $Na_2SO_4$ and the solvent is evaporated under reduced pressure. Crystallization in a toluene/petroleum ether mixture (1:1) provides colorless crystals.

Yield: 72%.

$^1$H NMR (300 MHz, $CDCl_3$) δ 3.76 (s, 8H), 1.67 (s, 8H), 1.20 (s, 24H); $^{13}$C NMR (75 MHz, $CDCl_3$) δ 99.8 (2C), 63.7 (4C), 54.5 (4C), 51.3 (4C), 43.2 (1C) 32.4 (8C).

ESI-HRMS m/z [M+H]$^+$; calc: 411.3217, found: 411.3217.

Preparation of the bTbK

To a solution of the diamine (0.50 g, 1.2 mmoL) in 20 mL of $CH_2Cl_2$ we added, at 0° C., a solution of m-CPBA (1.5 eq., 1.8 mmoL) in 10 mL of $CH_2Cl_2$. The mixture was stirred for 1 h at room temperature. The mixture was washed successively with a 10% solution of $NaHCO_3$ (10 mL), a solution (0.1 N) of HCl and 10 mL of water. The organic solution was dried on Na2SO4 then the solvent was evaporated under reduced pressure. The bTbK was purified by chromatography on a silica gel column with a $CH_2Cl_2$/EtOH (98:2) mixture as the eluent. Recrystallization in a pentane/diethyl ether (50:50) mixture provided slightly orange crystals of bTbK.

Yield: 50%.

ESI-HRMS m/z [M+H]$^+$; found: 441, calculated: 440.

X-Ray Diffraction Analysis of the bTbK

Figure 5:
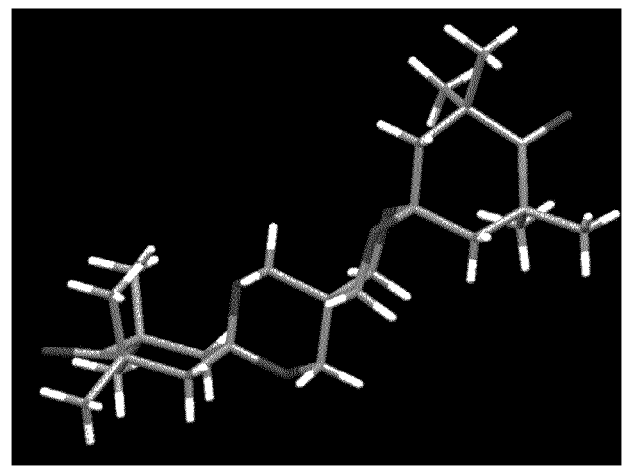
FIG. 5: Structure of bTbK determined by X-ray diffraction.

An x-ray diffraction analysis enabled the exact geometry of the bTbK to be determined (FIG. 5). The geometry of the bTbK determined by x-ray diffraction provided the following data regarding the disposition of the two nitroxide units:

$D_{O-O}$=13 Å, $D_{N-N}$=10.7 Å which corresponds to an average distance of 11.8 Å between the two lone electrons of the two nitroxide units.

The angle created by the nodal plans of the aminoxyl groups of the two nitroxide units was 82°.

Use of bTbK as a Polarizing Agent in DNP. Application to the Polarization of $^{13}$C Urea. Comparison of the Performances of bTbK and TOTAPOL.

DNP experiments using bTbK as the polarizing agent have been conducted in a magnetic field of 5 T, which corresponds to a Larmor frequency of 140 GHz for e$^-$ and 211 GHz for $^1$H. The polarization of the $^1$H was detected after its transfer to the $^{13}$C of urea whose NMR signal was recorded. The experiment was conducted at 93 K in a DNP/NMR spectrometer equipped with a triple-resonance cryogenic MAS sensor (e$^-$, $^1$H and $^{13}$C). The sample was irradiated using a gyrotron capable of producing high-power (>10 mW) millimetric waves at a frequency of 139.662 GHz. The 5 T superconducting magnet was equipped with a superconducting deflecting coil which allowed field scanning of ±750 G, in order to adjust the magnetic field to observe maximum polarization. The samples for DNP were prepared from solutions of 9 mM in bTbK and 2M in urea labeled with $^{13}$C in a $d_6$-DMSO/$D_2$O/$H_2$O (77/17/6) mixture. The high concentration of $^{13}$C-urea enabled optimization of NMR detection and observation of the NMR signal in a reasonable timeframe in the absence of polarization.

Figure 6:
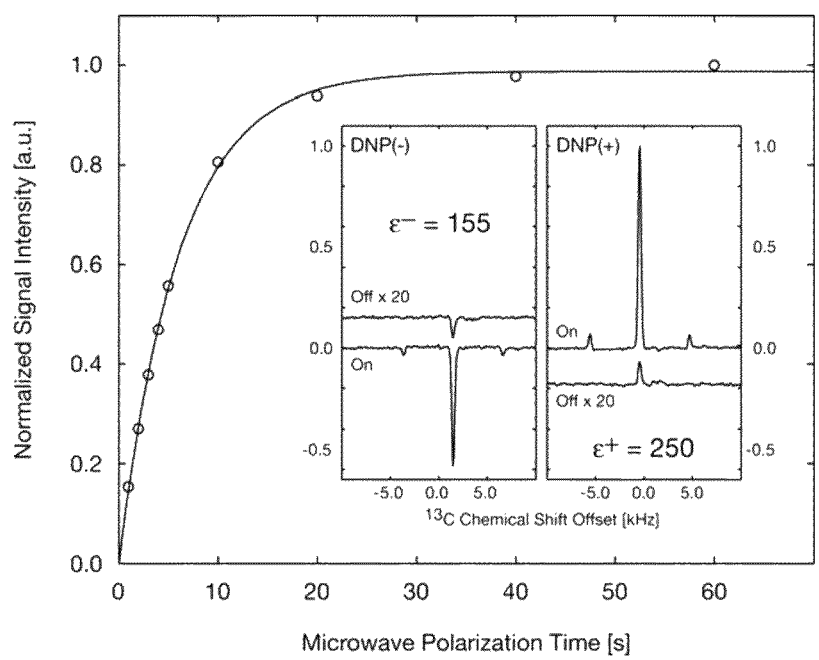
FIG. 6: Growth curve of the polarization of the medium's $^1$H in the presence of bTbK, recorded for the magnetic field value corresponding to positive polarization (DNP(+)). The polarization of the $^1$H is detected indirectly through the $^{13}$C urea signal through a sequence of cross polarization. Shown in the boxes are the spectra with or without irradiation for field values corresponding to DNP(+) and DNP(−).

A typical growth curve of the polarization of the $^1$H of the medium is given in FIG. 6, along with the NMR spectra recorded with or without irradiation at fields corresponding to the maximums of positive polarizations DNP(+) and negative polarizations DNP(-). The polarization of the $^1$H of the medium was monitored by transferring it by a sequence of cross polarization with $^{13}$C of urea. At a temperature of 93 K, the polarization growth time constant was 7 s and the stationary state achieved corresponded to a growth factor $\epsilon^+=250$ for positive polarizations, for an irradiation strength on the order of 2.5 W.

Under the same experimental conditions, TOTAPOL (R. G. Griffin et al: J. Am. Chem. Soc., 128, 11385-11390, 2006; J. Chem. Phys., 128, 052302-1/052302-17, 2008), which was, to date, the highest performing dinitroxide-type biradical in this type of experiment, showed a $\epsilon^+$ of 180.

Figure 7:
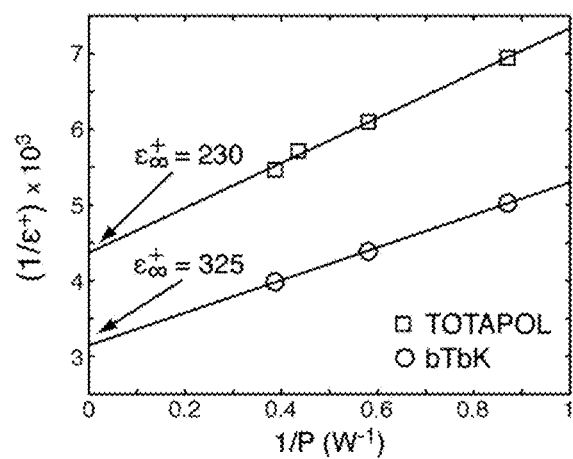
FIG. 7: Variation as a function of irradiation strength and enhancement of stationary maximum polarization ($\epsilon^+$) for the bTbK and the TOTAPOL recorded under the same experimental conditions.

The difference in efficiency between bTbK and TOTAPOL also translates to the polarization growth coefficient value for these two polarizing agents when the irradiation strength tends towards infinity (FIG. 7). The values found for $\epsilon_\infty^+$ were 230 and 325 for TOTAPOL and bTbK, respectively.

These experiments demonstrate the superiority of bTbK with respect to the other di-TEMPO type biradicals tested previously. The polarization growth factors measured with bTbK are approximately 1.4 times greater than those measured with TOTAPOL despite a less good solubility in water which limited its performance.

The invention claimed is:

1. A dinitroxide-type biradical compound comprising:
a rigid linkage between the two nitroxide units that maintains a specific orientation and distance between the two aminoxyl groups of these units, said rigid linkage being an odd number of spiranic bonds, wherein the dinitroxide-type biradical compounds are of the general formula:

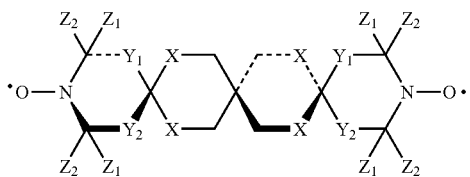

in which X is a single bond between the atoms n−1 and n+1, or O, N, N(O), S, S(O), SO2, or a (C1-C4) alkyl chain,
in which Y1 is a single bond between the atoms n−1 and n+1, or O, N, N(O), S, S(O), SO2, or a (C1-C4) alkyl chain,
in which Y2 is a single bond between the atoms n−1 and n+1, or O, N, N(O), S, S(O), SO2, or a (C1-C4) alkyl chain,
in which Z1=—R1 or —R1-R2 and Z2=—R1 or —R1-R2, where R1 is selected from the group consisting of a chain of (C1-C17) alkyl, cycloalkyl, heterocycloalkyl, spirocycloalkyl, spiroheterocycloalkyl, alkenyl, alkynyl, (C6-C18) aryl, and R2 is selected from the group consisting of H, hydroxyl (—OH), primary amine (—NH2), secondary amine (—NH), tertiary amine (—N), ammonio (—N$^+$), amine oxide (—NO), carboxyl (—COOH), sulfanyl (—SH), polyethylene-glycol (CH2-CH2-O)n-CH2X, X being OH or NH2), sulfinyl (—SO), sulfonyl (—SO2), sulfonato (—SO$_3^-$), phosphono (—PO3H2, —PO3R2 where R is (C1-C17) alkyl or (C6-C18) aryl), phosphoryl (—P(O)R2 where R—(C1-C17) alkyl, (C6-C18) aryl), phosphonio (—P$^+$), phosphoric ester (—O—PO$_3^-$), wherein
the dinitroxide-type biradical compounds further include the addition of at least one chemical group that facilitates solubility, selected from among the functions and groups of hydroxyl (—OH), primary amine (—NH2), secondary amine (—NH), tertiary amine (—N), ammonio (—N$^+$), amine oxide (—NO), carboxyl (—COOH), sulfonyl (—SH), polyethylene-glycol (CH2-CH2-O)n-CH2X, where X is OH or NH2) sulfinyl (—SO), sulfonyl (—SO2), sulfonato (—SO$_3^-$), phosphono (—PO3H2, —PO3R2 where R is (C1-C17) alkyl or (C6-C18) aryl), phosphoryl (—P(O)R2 where R is (C1-C17) alkyl or (C6-C18) aryl), phosphonio (—P$^+$), phosphoric ester (—O—PO$_3^-$).

2. The dinitroxide-type biradical compound of claim 1, in which the linkage between the two nitroxide units enables a stable conformation to be obtained in which the nodal plans of the aminoxyl groups of these two units create between them an angle between 65° and 115°, inclusive.

3. The dinitroxide-type biradical compound of claim 1, in which the linkage between the two nitroxide units enables the nitrogen atoms of the aminoxyl groups of the nitroxide units to be maintained at a distance of between 3 and 16 A.

4. The dinitroxide-type biradical compound of claim 1, in which the nitroxide units are selected from units of piperidinoxyl, pyrrolidinoxyl, imidazolinoxyl, imidazolidinoxyl, oxazolidinoxyl and nitronylnitroxide.

5. The dinitroxide-type biradical compound of claim 1, characterized by the addition of at least one photosensitizing group selected from thioxanthone, benzoin, benzyl dimethyl acetal or benzophenone.

6. The dinitroxide-type biradical compound of claim 1, characterized by the addition of at least one chemical group reactive with respect to the groups —SH, —NH2, —NH—, —OH, —COOH, hydroxyaryl (ArOH) such as:

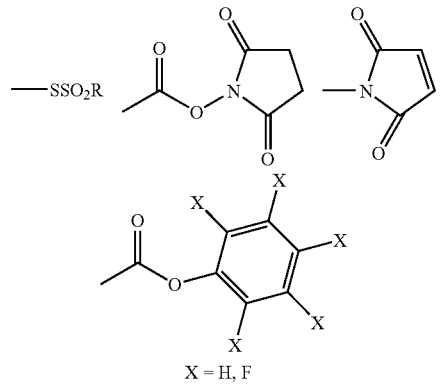

X = H, F

7. The dinitroxide-type biradical compound of claim 1, characterized by their conjugation to biomolecules selected from proteins, ribosomes, lipids, saccharides, DNA, RNA.

8. The dinitroxide-type biradical compound of claim 1, which are isotopically labeled with an atom selected from Deuterium ($^2$H), Carbon 13 ($^{13}$C) and Nitrogen 15 ($^{15}$N).

9. A dinitroxide-type biradical compound comprising:
a rigid linkage between the two nitroxide units that maintains a specific orientation and distance between the two aminoxyl groups of these units, said rigid linkage being an odd number of spiranic bonds, wherein the dinitroxide-type biradical compounds are of the general formula:

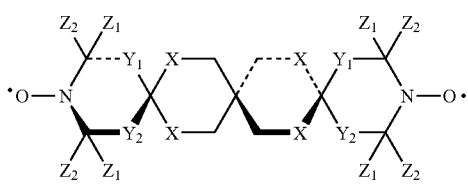

in which X is a single bond between the atoms n−1 and n+1, or O, N, N(O), S, S(O), SO2, or a (C1-C4) alkyl chain, in which Y1 is a single bond between the atoms n−1 and n+1, or O, N, N(O), S, S(O), SO2, or a (C1-C4) alkyl chain, in which Y2 is a single bond between the atoms n−1 and n+1, or O, N, N(O), S, S(O), SO2, or a (C1-C4) alkyl chain, in which $Z_1$ and $Z_2$ form together a (C4-C17) spirocycloalkyl or spiroheterocycloalkyl.

10. The dinitroxide-type biradical compound of claim 9, further including the addition of at least one photosensitizing group selected from thioxanthone, benzoin, benzyl dimethyl acetal or benzophenone.

11. The dinitroxide-type biradical compound of claim 9, which are isotopically labeled with an atom selected from Deuterium ($^2$H), Carbon 13 ($^{13}$C) and Nitrogen 15 ($^{15}$N).

12. The dinitroxide-type biradical compound of claim 1, further including the addition of at least one photosensitizing group selected from thioxanthone, benzoin, benzyl dimethyl acetal or benzophenone.

13. The dinitroxide-type biradical compound of claim 1, which are isotopically labeled with an atom selected from Deuterium ($^2$H), Carbon 13 ($^{13}$C) and Nitrogen 15 ($^{15}$N).

* * * * *